US010143530B2

(12) United States Patent
Liou et al.

(10) Patent No.: US 10,143,530 B2
(45) Date of Patent: Dec. 4, 2018

(54) MEMBRANE FOR PROTECTING INTRAOCULAR TISSUES AND THE PROTECTION METHODS USED THEREOF

(71) Applicants: Industrial Technology Research Institute, Hsinchu (TW); National Taiwan University Hospital, Taipei (TW)

(72) Inventors: Yu-Bing Liou, Hsinchu (TW); Hsiu-Ying Wang, New Taipei (TW); Hsin-Yi Hsu, Taoyuan (TW); Wei-Li Chen, Taipei (TW); Chin-Tsung Huang, Hsinchu (TW); Hsin-Hsin Shen, Zhudong Township (TW)

(73) Assignees: INDUSTRIAL TECHNOLOGY RESEARCH INSTITUTE, Hsinchu (TW); NATIONAL TAIWAN UNIVERSITY HOSPITAL, Taipei (TW)

(*) Notice: Subject to any disclaimer, the term of this patent is extended or adjusted under 35 U.S.C. 154(b) by 34 days.

(21) Appl. No.: 15/211,141

(22) Filed: Jul. 15, 2016

(65) Prior Publication Data

US 2017/0172686 A1    Jun. 22, 2017

(30) Foreign Application Priority Data

Dec. 18, 2015    (TW) .............................. 104142632 A (51) Int. Cl.
*A61B 90/00* (2016.01)
*A61F 9/007* (2006.01)
(Continued)

(52) U.S. Cl.
CPC .......... *A61B 90/04* (2016.02); *A61F 9/00745* (2013.01); *A61L 31/044* (2013.01);
(Continued)

(58) Field of Classification Search
CPC ..... A61B 9/007; A61B 9/00745; A61B 90/04; A61L 31/041; A61L 31/044;
(Continued)

(56) References Cited

U.S. PATENT DOCUMENTS

| 4,170,661 A | 10/1979 | Knight et al. |
| 4,452,600 A | 6/1984 | Schachar |

(Continued)

FOREIGN PATENT DOCUMENTS

| CN | 101132818 A | 2/2008 |
| CN | 102580166 A | 7/2012 |

(Continued)

OTHER PUBLICATIONS

Li et al., "Fabrication and Characterization of Chitosan-Collagen Crosslinked Membranes for Corneal Tissue Engineering," Journal of Biomaterials Science, Polymer Edition, vol. 25, No. 17, 2014, pp. 1962-1972 (12 pages total).

(Continued)

*Primary Examiner* — Howie Matthews
(74) *Attorney, Agent, or Firm* — Birch, Stewart, Kolasch & Birch, LLP (57) ABSTRACT

According to embodiments, a membrane with a flat or curved surface is provided for protection of intraocular tissues. The membrane can be used to cover the cornea for protecting corneal endothelial cells, to cover the anterior and posterior surface of the iris, or to cover the surface of the posterior capsule for separating the intraocular tissues. The membrane has a layered structure, which is composed of a collagen and a hydrophilic biopolymer or an organic polymer material. In particular, the membrane has high transparency and high water retention in a wet state.

16 Claims, 7 Drawing Sheets

(51) Int. Cl.
  *A61L 31/04* (2006.01)
  *A61L 31/06* (2006.01)
  *A61L 31/12* (2006.01)
  A61L 27/16 (2006.01)
  A61L 27/18 (2006.01)
  A61L 27/24 (2006.01)

(52) U.S. Cl.
  CPC ............. *A61L 31/048* (2013.01); *A61L 31/06* (2013.01); *A61L 31/129* (2013.01); *A61B 2090/0427* (2016.02); *A61B 2090/0445* (2016.02); *A61B 2090/0472* (2016.02); *A61B 2090/08021* (2016.02); *A61L 27/16* (2013.01); *A61L 27/18* (2013.01); *A61L 27/24* (2013.01); *A61L 2430/16* (2013.01)

(58) Field of Classification Search
  CPC .... A61L 2430/16; A61F 2/0214; A61F 2/142; A61F 9/007; A61F 9/00745; A61F 2/14
  See application file for complete search history.

(56) References Cited

U.S. PATENT DOCUMENTS

| | | | |
|---|---|---|---|
| 6,123,081 | A | 9/2000 | Durette |
| 6,192,888 | B1 | 2/2001 | Chandler et al. |
| 6,220,246 | B1 | 4/2001 | Chandler et al. |
| 7,563,396 | B2 | 7/2009 | Fuerst et al. |
| 7,811,267 | B2 | 10/2010 | Norrby et al. |
| 7,883,693 | B2 | 2/2011 | Sehl et al. |
| 7,985,208 | B2 * | 7/2011 | Christensen ............... A61F 2/14 424/428 |
| 8,466,203 | B2 | 6/2013 | Paik et al. |
| 8,628,572 | B2 | 1/2014 | Soker et al. |
| 2004/0039399 | A1 | 2/2004 | Norrby et al. |
| 2004/0049187 | A1 * | 3/2004 | Burnett ................... A61L 15/32 606/52 |
| 2005/0067287 | A1 | 3/2005 | Fuerst et al. |
| 2008/0269119 | A1 | 10/2008 | Griffith et al. |
| 2013/0204363 | A1 | 8/2013 | Aksan et al. |
| 2014/0074074 | A1 | 3/2014 | Dick et al. |
| 2014/0377326 | A1 | 12/2014 | Niu et al. |
| 2016/0325009 | A1 * | 11/2016 | Cohn ................... A61L 24/001 |

FOREIGN PATENT DOCUMENTS

| | | |
|---|---|---|
| CN | 104144715 A | 11/2014 |
| EP | 1 132 065 A1 | 9/2001 |
| TW | 200740416 A | 11/2007 |
| TW | 200925700 A | 6/2009 |
| WO | WO 03/059391 A2 | 7/2003 |
| WO | 20111097619 A2 | 8/2011 |
| WO | 2013/040559 A1 | 3/2013 |

OTHER PUBLICATIONS

Liu et al., "Crosslinked Collagen-Gelatin-Hyaluronic Acid Biomimetic Film for Cornea Tissue Engineering Applications," Materials Science and Engineering C, vol. 33, No. 1, 2013 (published online Aug. 19, 2012), pp. 196-201.
Long et al., "Improving the Medhanical Properties of Collagen-Based Membranes Using Silk Fibroin for Corneal Tissue Engineering," Journal of Biomedical Materials Research Part A,vol. 103, Issue 3, Mar. 2015 (published online Jul. 15, 2014), pp. 1159-1168.
Shoulders et al., "Collagen Structure and Stability," Annu Rev Biochem., vol. 78, 2009, pp. 929-958.
Taiwanese Office Action and Search Report, dated Aug. 16, 2017, for Taiwanese Application No. 104142632.
Deng et al., "Collagen and glycopolymer based hydrogel for potential corneal application", Acta Biomaterialia, vol. 6, 2010, pp. 187-194.
Feistritzer et al., "Endothelial barrier protection by activated protein C through PAR1-dependent sphingosine 1-phosphate receptor-1 crossactivation", Blood, vol. 105, No. 8, Apr. 15, 2005, pp. 3178-3184.
Fuchsluger et al., "Corneal Endothelial Cells Are Protected from Apoptosis by Gene Therapy", Human Gene Therapy, vol. 22, May 2011, pp. 549-558.
Lawrence et al., "Silk film biomaterials for cornea tissue engineering", Biomaterials, vol. 30, 2009, pp. 1299-1308.
Maltese et al., "Novel polysaccharides-based viscoelastic formulations for ophthalmic surgery: Rheological characterization", Biomaterials, vol. 27, 2006, pp. 5134-5142.
Miyashita et al., "Collagen-Immobilized Poly(Vinyl Alcohol) as an Artificial Cornea Scaffold that Supports a Stratified Corneal Epithelium", Journal of Biomedical Materials Research—Part B Applied Biomaterials, vol. 76, No. 1, 2006, pp. 56-63.
Rafat et al., "PEG-stabilized carbodiimide crosslinked collagen-chitosan hydrogels for corneal tissue engineering", Biomaterials, vol. 29, 2008, pp. 3960-3972.
Richard et al., "Corneal Endothelial Cell Loss After Cataract Extraction by Using Ultrasound Phacoemulsification Versus a Fluid-based System", Cornea, vol. 27, No. 1, Jan. 2008, pp. 17-21.
Sionkowska et al., "Collagen-synthetic polymer interactions in solution and in thin films", Journal of Molecular Liquids, vol. 145, 2009, pp. 135-138.
Storr-Paulsen et al., "The influence of viscoelastic substances on the corneal endothelial cell population during cataract surgery: a prospective study of cohesive and dispersive viscoelastics", Acta Ophthalmologica Scandinavica, vol. 85, 2007, pp. 183-187.
Jiang-Ping et al., "Biocompatibility Assessment of Chitosan-collagen Membrane at Different Intracorneal Implantation Positions," Journal of Clinical Rehabilitative Tissue Engineering Research, vol. 14, No. 34, Aug. 20, 2010, pp. 6319-6322, with an English abstract.
Taiwanese Office Action and Taiwanese Search Report, dated Feb. 2, 2017, for Taiwanese Application No. 104142632.

* cited by examiner

MEMBRANE FOR PROTECTING INTRAOCULAR TISSUES AND THE PROTECTION METHODS USED THEREOF

CROSS REFERENCE TO RELATED APPLICATIONS

The application is based on, and claims priority from, Taiwan Application Serial Number 104142632, filed on Dec. 18, 2015, the disclosure of which is hereby incorporated by reference herein in its entirety.

TECHNICAL FIELD

The disclosure relates to a membrane for protecting intraocular tissues and a method for protecting intraocular tissues.

BACKGROUND

In various types of intraocular surgery, the degree of damage done to the corneal endothelial cells is a determining factor in assessing the success of the surgery. In particular, the air in the anterior capsule and the posterior capsule of the iris should be separated during intraocular surgery, in order to avoid reducing the success rate of the surgery due to air circulation. Furthermore, displacement of the vitreous should be avoided in order to prevent the vitreous from remaining in the anterior capsule and permanently damaging the anterior capsule tissues. Moreover, in cataract surgery, it is important to prevent shards of the crystalline lens from shifting during surgery, in order to avoid the need for a second surgery to repair the results of the shards of the crystalline lens having fallen into the posterior capsule.

A method is currently being used for preventing the corneal endothelial cells from being damaged, preventing air from entering the anterior capsule, preventing the posterior capsule of the iris from flowing, and preventing the vitreous or shards of the crystalline lens from shifting. The current method includes injecting injectable gel-like ocular viscoelastic devices (OVDs) into the intraocular tissues and then removing the ocular viscoelastic devices. The ocular viscoelastic devices, which have a gel-type structure similar to that of the vitreous, are also known as artificial vitreous. The ocular viscoelastic devices have characteristics that make them easy to adhere to the surface of the corneal endothelial layer, easy to separate from the intraocular tissues, convenient to inject, and easy to remove. However, there are risks to using the ocular viscoelastic devices in cataract surgery case, including: (1) insufficient protection and separating properties; (2) it is not easy to determine the location of the ocular viscoelastic devices and/or to determine whether the ocular viscoelastic devices remain in the intraocular tissues: (3) the ocular viscoelastic devices can easily become lost or taken away by drainage equipment; and (4) it is difficult to construct a complete plane barrier using ocular viscoelastic devices.

Therefore, the membrane for protecting the corneal endothelial cells should have the following characteristics: (1) they should be one-piece, resulting in being implanted or removed conveniently; (2) they should have a clear boundary, resulting in being able to conveniently determine the location of the membrane; (3) they should have high transparency, so that the membrane does not impact surgical use; (4) they should be soft and malleable; and (5) they should be tougher than ocular viscoelastic devices.

Accordingly, a novel transparent membrane for protecting the corneal endothelial cells and the intraocular tissues which overcomes the above difficulties and inconveniences is desired.

SUMMARY

According to embodiments of the disclosure, the disclosure provides a membrane for protecting intraocular tissues. The membrane for protecting intraocular tissues includes a layered structure composed of a collagen and a hydrophilic polymer, wherein the collagen is strip-shaped and has a fiber length between about 1.5 mm and 50 mm, and wherein the membrane has a diameter between about 6 mm and 16 mm, and the membrane in a dry state has a first thickness between about 5 μm and 100 μm.

According to another embodiment of the disclosure, the disclosure also provides a method for protecting corneal endothelial cells. The method for protecting corneal endothelial cells includes providing the aforementioned membrane for protecting intraocular tissues, wherein the membrane has a curved surface, and the curved surface has a radius of curvature from about 6 mm to 8 mm; allowing the membrane for protecting intraocular tissues to be swollen after swelling with water, obtaining a transparent membrane having a thickness between about 50 μm and 300 μm; and, disposing the transparent membrane in an anterior capsule to cover corneal endothelial cells.

According to yet another embodiment of the disclosure, the disclosure also provides a method for protecting intraocular tissues. The method for protecting intraocular tissues includes providing the aforementioned membrane for protecting intraocular tissues: allowing the membrane for protecting intraocular tissues to be swollen after swelling with water, obtaining a transparent membrane having a thickness between about 50 μm and 300 μm; and, disposing the transparent membrane in front of the posterior capsule of a crystalline lens.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

The disclosure discloses a membrane for protecting intraocular tissues, and the membrane can be used to protect corneal endothelial cells or to separate the anterior tissues or posterior tissues of the iris. The membrane exhibits high transparency and high water retention. During an ophthalmologic procedure, the membrane can be used to cover the bottom of the corneal endothelium, to be disposed at the front or rear of the iris for protecting the corneal endothelial cells, or to separate the anterior tissue of the iris from the posterior tissues of the iris. The membrane of the disclosure is obtained by subjecting a collagen and a hydrophilic biodegradable polymer (or an organic polymer) to a blending process. Since the collagen has a longer fiber length, the membrane can have a multi-layered structure, resulting in the membrane exhibiting a high water-absorption ability and a high suture pull-out strength. Since the membrane is a layered structure composed of a collagen and a hydrophilic polymer, the membrane of the disclosure can exhibit a high light transmittance, a high water retention, and a high tensile strength after swelling with water (i.e. wet film). In particular, the degree of adaptation between the membrane and the cornea can be increased due to the high water retention of the membrane. In addition, the elasticity and flexibility of the membrane is also proportional to the water retention of the membrane. Moreover, the membrane of the disclosure can be applied to ophthalmology, surgical use, or tissue engineering.

The membrane of the disclosure includes a layered structure composed of a collagen and a hydrophilic polymer (or an organic polymer), wherein the collagen is strip-shaped and has a fiber length between about 1.5 mm and 50 mm, such as between about 15 mm and 30 mm. The collagen fibers can be present in a tiny fiber or molecular configuration and can be in a fully extended state due to the intramolecular charge repulsion and the hydrogen bond interaction between the collagen and water, when placed in an acid solution. Meanwhile, due to the fiber length being longer than 1.5 mm (i.e. strip-shaped fiber, rather than flocculent fiber), the collagen fiber can be stacked regularly to have a long fibrous morphology during drying, resulting in a membrane having a layered structure.

On the other hand, the collagen and the polymer can be stacked regularly to form the layered structure due to the hydrogen bonds between the collagen and the polymer. Due to the presence of the polymer (especially the polymer with high molecular weight), the collagen in the membrane has a long fibrous morphology, resulting in enhancing the mechanical strength of the layered structure of the membrane.

Namely, due to the self-assembly mechanism and the specific fiber length of the collagen, and the presence of the hydrophilic polymer, the strength of the membrane can meet the desired strength requirements. Therefore, a fiber reinforced composite membrane can be obtained by blending the collagen and the hydrophilic polymer, wherein the collagen in the membrane not only serves a non-woven fiber mesh but also enhances the anisotropic strength of the membrane, resulting in the membrane exhibiting high tensile strength, high elasticity, and high flexibility.

According to embodiments of the disclosure, the hydrophilic polymer can be a transparent biodegradable polymer, such as chitosan, gelatin, hyaluronic acid, polyethylene glycol (PEG), polyethylene oxide (PEO), polyvinyl alcohol (PVA), polyvinylpyrrolidone (PVP), or a combination thereof. The hydrophilic polymer can have a molecular weight (such as a weight-average molecular weight) between about 300 and 400,000 (such as between about 300 and 10,000, between about 30,000 and 80,000, and between about 100,000 and 400,000). The degradation rate of the membrane can be controlled by modifying the molecular weight of the hydrophilic polymer. For example, usage of hydrophilic polymers with a relatively low molecular weight (such as between 300 and 10,000) results in a high degradation rate of the composite material. On the other hand, usage of hydrophilic biodegradable polymers with a relatively high molecular weight (such as between 100,000 and 400.000) results in a slow degradation rate of the composite material.

Furthermore, the degradation rate of the membrane can be controlled by means of the cross-linking process. For example, the degradation rate of the membrane can be controlled by increasing or reducing the reaction time of the cross-linking process, wherein the reaction time can be from several minutes to 3 hours. When the reaction time is relatively short, the membrane has a relatively low cross-linking degree and a relatively high degradation rate. When the reaction time is relatively long, the membrane has a relatively high cross-linking degree and a relatively low degradation rate. Moreover, the transparency, water retention, and curvature of the membrane can be controlled by adjusting the cross-linking degree. For example, in order to match the curvature of the cornea, the membrane of the disclosure is shaped to have a curved surface that is similar to the cornea during the cross-linking process.

According to embodiments of the disclosure, the weight ratio between the collagen and the hydrophilic polymer can be from about 1:3 to 9:1, such as from 1:5 to 5:1, or from 1:3 to 3:1. When the weight ratio of the collagen and hydrophilic polymer is too low, the membrane is relatively brittle and apt to dissolve in water (rather than forming a film) due to the absence of collagen fibers. On the other hand, when the weight ratio of the collagen and hydrophilic polymer is too high, the light transmittance and the water retention of the membrane are reduced.

Figure 4:
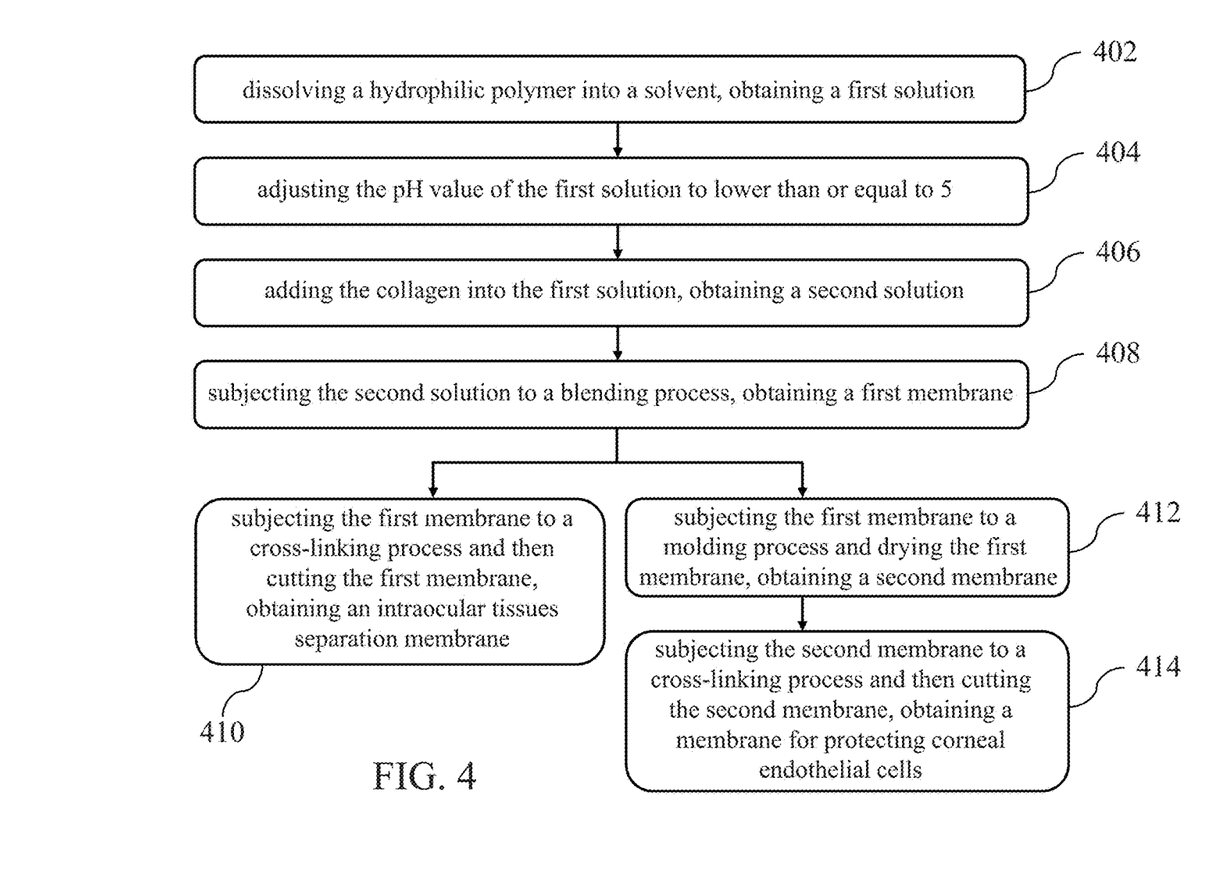
FIG. 4 is a flow chart illustrating a method for fabricating a membrane according to an embodiment of the disclosure.

According to embodiments of the disclosure, the method for fabricating the membrane of the disclosure for protecting intraocular tissues can include the following steps, as shown in FIG. 4. First, a hydrophilic polymer is dissolved into a solvent, obtaining a first solution (step 402). Next, the pH value of the first solution is adjusted to be lower than or equal to 5, such as lower than or equal to 3 (step 404). The subsequently added collagen can be completely dissolved in the solvent when the first solution has a pH value lower than or equal to 5. When the pH value of the first solution is greater than 5, the collagen will be separated out rather than dissolving in the solvent. Next, a collagen is added into the first solution, obtaining a second solution (step 406). In particular, the collagen is strip-shaped and has a fiber length between about 1.5 mm and 50 mm. Next, the second solution is subjected to a blending process, obtaining a first membrane (step 408). Since there is a high miscibility between the collagen and the hydrophilic polymer, the blending process can be a biaxial stretching process or solvent casting, and the collagen can be blended with one or more than one hydrophilic biodegradable polymers.

Next, after step 408, the first membrane can be subjected to a cross-linking process and then cut to obtain an intraocular tissues separation membrane (step 410), wherein the shape of the separation membrane is circular with a diameter from about 6 mm to 16 mm. According to an embodiment of the disclosure, the first membrane is subjected to a molding process (step 412). The molding process includes swelling the first membrane with water, covering the first membrane to a mold with a curved surface, and drying the first membrane to obtain a second membrane having a curved surface with a radius of curvature from about 6 mm to 8 mm. Step 412 can be performed immediately after step 408. Next, the second membrane is subjected to a cross-linking process and then cut to obtain a membrane for protecting cornea.

According to embodiments of the disclosure, after obtaining the membrane, the membrane can be subject to a cross-linking process so that the hydrophilic polymer and/or the collagen undergoes a cross-linking reaction. The cross-linking reaction can effectively increase the degradation period of the composite material. The cross-linking process can be a chemical cross-linking process with a cross-linking agent. The cross-linking agent can include formaldehyde, glutaraldehyde, glyoxal, malondialdehyde, succinyl dialdehyde, phthalaldehyde, dialdehyde starch, polyacrolein, polymethacrolein, or a combination thereof. Due to the use of aldehyde as a cross-linking agent, the collagen of the membrane can be further cross-linked via the chemical cross-linking process.

According to another embodiment of the disclosure, the cross-linking process can be a physical cross-linking process. In the physical cross-linking process, the membrane is irradiated by radiation, wherein the radiation can be an ultraviolet light, or a Gamma ray. When the membrane is irradiated with ultraviolet light, the collagen and hydrophilic biodegradable polymer of the membrane can be cross-linked further. The cross-linking reaction can have a reaction time from about 10 minutes to several hours. The cross-linking degree of the membrane is proportional to the reaction time of the cross-linking reaction, and the degradation rate of the membrane is inversely proportional to the reaction time of the cross-linking reaction.

Figure 2A:
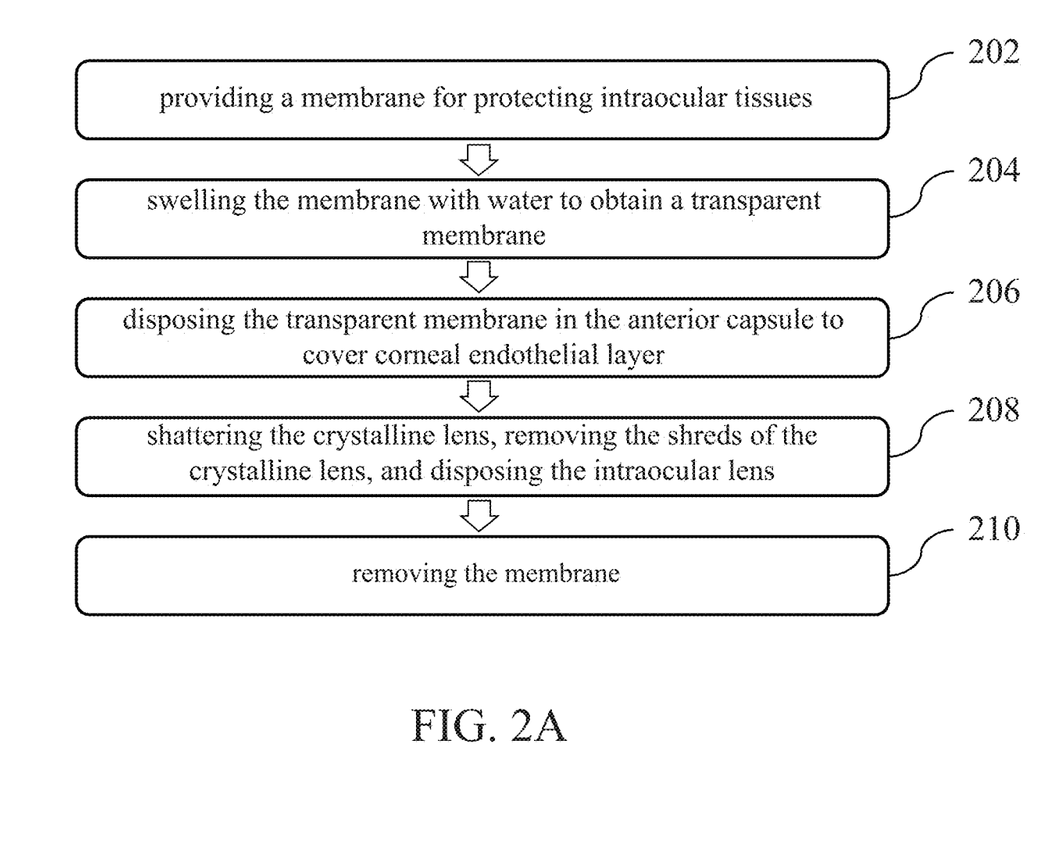
FIG. 2A is a flow chart illustrating a method for protecting corneal endothelial cells according to an embodiment of the disclosure.
Figure 2B:
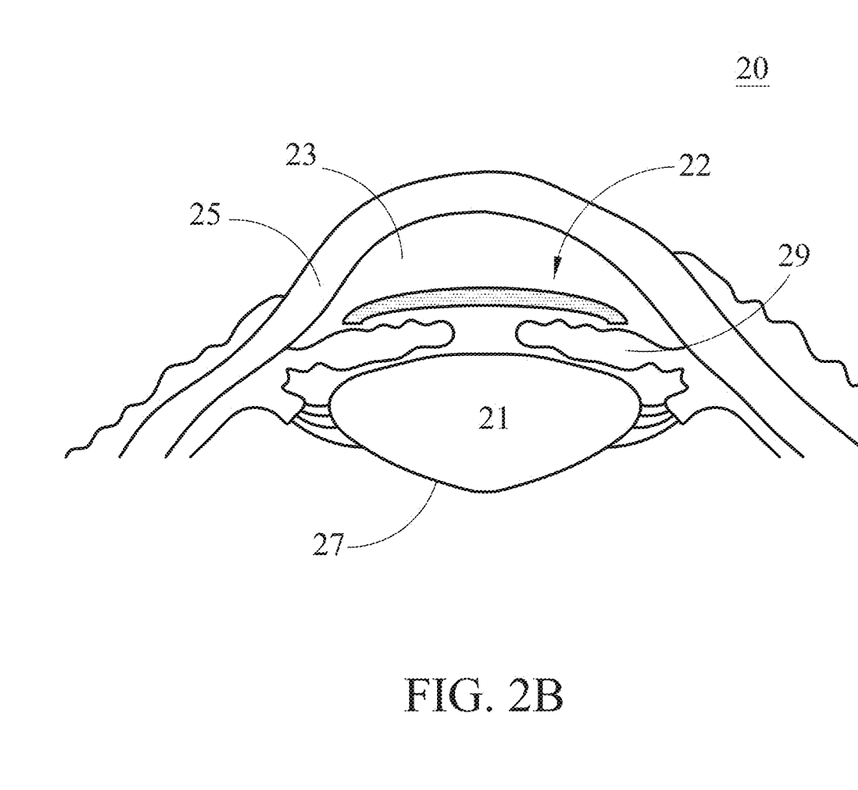
FIG. 2B is a schematic diagram showing the location of the membrane used in step 206 of the method for protecting corneal endothelial cells shown in FIG. 2A.

According to embodiments of the disclosure, the method for protecting corneal endothelial cells of the disclosure can include following steps as shown in FIG. 2A. First, a membrane with a curved surface for protecting intraocular tissues 22 is provided (step 202), wherein the membrane 22 includes a layered structure composed of a collagen and a hydrophilic polymer. The collagen is strip-shaped and has a fiber length between about 1.5 mm and 50 mm, and the membrane 22 has a diameter from about 6 mm to 16 mm. The membrane 22 in a dry state has a first thickness between 5 μm and 100 μm, and a curved surface of the membrane has a radius of curvature from 6 mm to 8 mm. Next, the membrane 22 is swelled with water to obtain a transparent membrane (step 204), wherein the transparent membrane has a second thickness from about 50 μm to 300 μm, and has a water retention greater than or equal to 80% and a light transmittance greater than or equal to 90%. Next, the moist transparent membrane 22 is disposed at an eye anterior capsule 23 to cover the corneal endothelial cells 25 (step 206) as shown in FIG. 2B. For example, the membrane of the disclosure can be used in the implantation process of the crystalline lens. After disposing the transparent membrane 22 at the eye anterior capsule 23 to cover corneal endothelial cells 25, the crystalline lens 21 is shattered by ultrasonic vibration, the shards of the crystalline lens 21 are removed, and the intraocular lens is disposed (step 208). Finally, the membrane 22 is removed (step 210), thereby completing the method for protecting corneal endothelial cells.

Figure 3A:
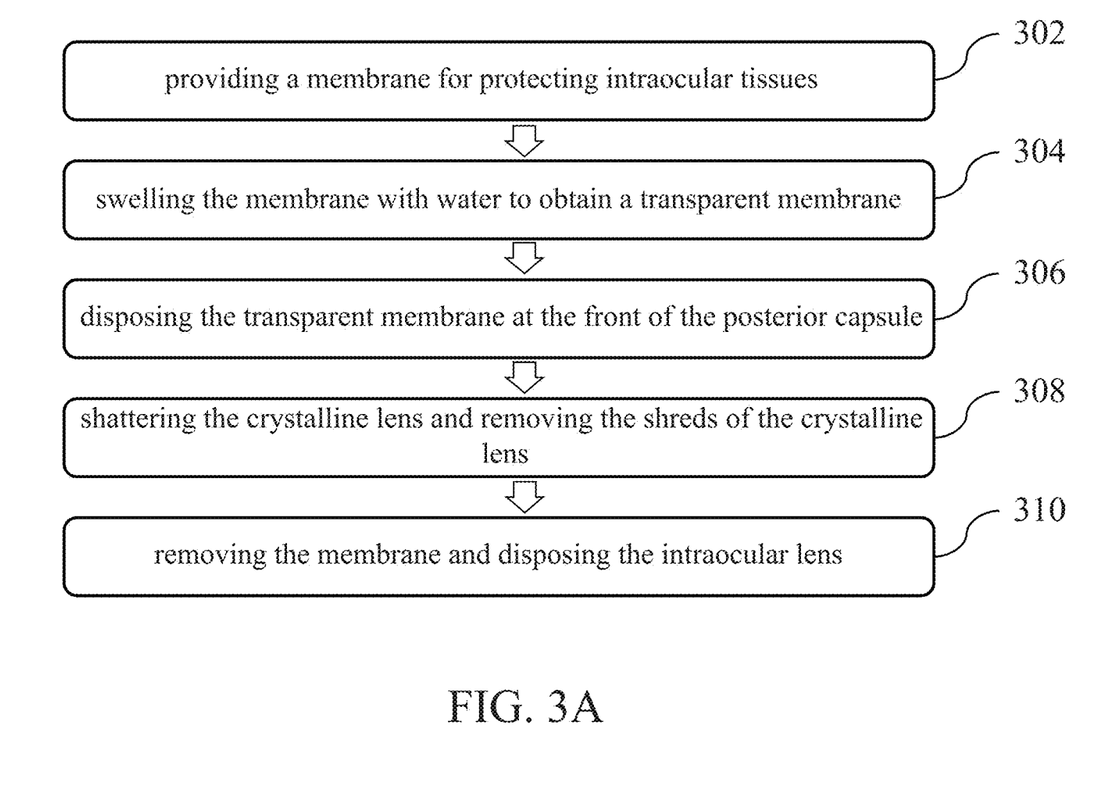
FIG. 3A is a flow chart illustrating a method for protecting intraocular tissues according to an embodiment of the disclosure.
Figure 3B:
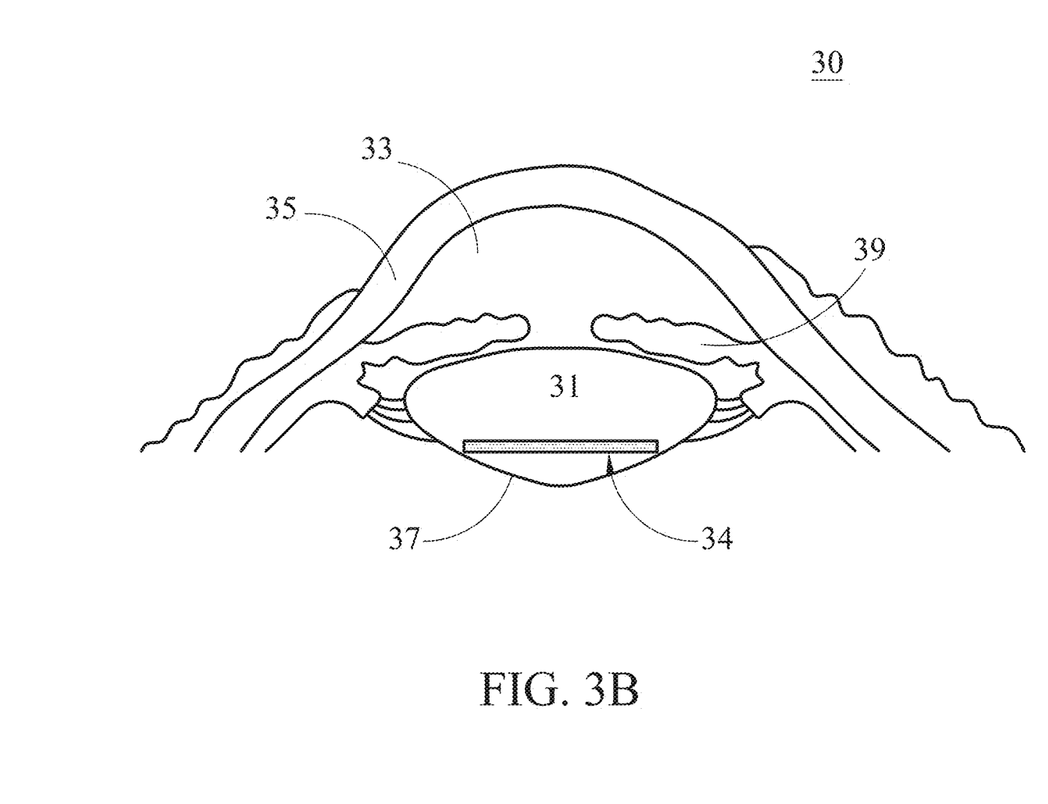
FIG. 3B is a schematic diagram showing the location of the membrane used in step 306 of the method for protecting intraocular tissues shown in FIG. 3A.

According to embodiments of the disclosure, the method for protecting intraocular tissues of the disclosure can include following steps as shown in FIG. 3A. First, a membrane 34 with a curved surface for protecting intraocular tissues is provided (step 302), wherein the membrane 34 includes a layered structure composed of a collagen and a hydrophilic polymer. The collagen is strip-shaped and has a fiber length between about 1.5 mm and 50 mm, and the membrane 34 has a diameter from about 6 mm to 16 mm. The membrane 34 in a dry state has a first thickness between about 5 μm and 100 μm. Next, the membrane 34 is swelled with water to obtain a transparent membrane (step 304), wherein the transparent membrane has a second thickness from about 50 μm to 300 μm, and has a water retention greater than or equal to 80% and a light transmittance greater than or equal to 90%. Next, the moist transparent membrane 34 is disposed at the front or rear of the iris or the front of the posterior capsule of a crystalline lens capsule 37 (step 306) of the eye 30 as shown in FIG. 3B. The membrane of the disclosure can be used in the phacoemulsification of the crystalline lens 31. For example, before performing the phacoemulsification, the membrane 34 is disposed at the front or rear of the iris or the front of the posterior capsule of a crystalline lens 37 for protecting the intraocular tissues. The crystalline lens 21 is shattered by ultrasonic vibration (step 308). Accordingly, the shards of the crystalline lens can be separated from the posterior capsule of a crystalline lens capsule 37 by the membrane 34, resulting in preventing the posterior capsule of a crystalline lens capsule 37 from being damaged by shards of the crystalline lens and further preventing the shards of the crystalline lens from falling into the vitreous (not shown). After removing the shards of the crystalline lens, the membrane 34 is removed (step 310), and the intraocular lens is implanted, thereby completing the method for protecting intraocular tissues.

In another embodiment of the disclosure, the plane transparent membrane 34 can be implanted for separating from the intraocular tissues during the phacoemulsification of the crystalline lens. For example, during the phacoemulsification of the crystalline lens via ultrasonic vibration, if a defect of the posterior capsule of the crystalline lens capsule is observed, the plane transparent membrane 34 can be disposed in front of the defect of the posterior capsule of the crystalline lens 37, for separating the shards of the crystalline lens shattered by ultrasonic vibration from the vitreous of the posterior capsule of the crystalline lens capsule 37. Therefore, the symptoms that are caused by shards of the crystalline lens falling into the vitreous from the defect of the posterior capsule of the crystalline lens capsule 37 can be avoided.

In yet another embodiment of the disclosure, the plane membrane 34 for separating from the intraocular tissues can be further used with the membrane 22 having a curved surface for protecting the corneal endothelial cells or the commercial ocular viscoelastic devices. For example, referring to FIGS. 2A-2B and 3A-3B simultaneously, the membrane 22 having a curved surface for protecting the corneal endothelial cells or the commercial ocular viscoelastic devices (OVD) can be used for protecting intraocular tissues in advance, and then the membrane for protecting intraocular tissues 34 can be separated from the intraocular tissues and avoiding the shards of the crystalline lens falling into the vitreous during or before the phacoemulsification of the crystalline lens. After removing the shards of the crystalline lens, the membrane for protecting intraocular tissues 34 is removed and the intraocular lens is implanted. After, the membrane 22 having a curved surface for protecting the corneal endothelial cells or the commercial ocular viscoelastic device (OVD) is removed, thereby completing the method for protecting corneal endothelial cells and separating from the intraocular tissues.

According to embodiments of the disclosure, the transparent membrane of the disclosure, such as the membrane 22 having a curved surface for protecting the corneal endothelial cells or the plane membrane 34 for separating from the intraocular tissues, can have a swelling ratio between about 2 and 15, a water retention greater than or equal to 80%, a light transmittance greater than or equal to 90%, and a suture pull-out strength between about 3 Mpa and 50 Mpa. Furthermore, the membrane of the disclosure in a dry state has a first thickness between about 5 μm and 100 μm. The membrane is a transparent membrane after swelling with water and the transparent membrane has a second thickness from 50 μm to 300 μm.

Below, exemplary embodiments will be described in detail with reference to the accompanying drawings so as to be easily realized by a person having ordinary knowledge in the art. The concept of the disclosure may be embodied in various forms without being limited to the exemplary embodiments set forth herein. Descriptions of well-known parts are omitted for clarity, and like reference numerals refer to like elements throughout.

Fabrication of the membrane for protecting intraocular tissues

EXAMPLE 1

First, 0.5 g of collagen (strip-shaped fiber with a fiber length about 15 mm), and 100 mL of an aqueous solution (pH<5) were added into a reaction bottle. Next, after the collagen was dissolved into the water, the solution was injected into a two-dimensional mold and dried at room temperature. Next, a part of the result was disposed in a chamber to undergo a cross-linking reaction and cut to obtain a membrane (I) with a diameter from 6 mm to 16 mm. Furthermore, another part of the result was also disposed into a mold (having a radius of curvature from 6 mm to 8 mm) after swelling with water, and then underwent a cross-linking reaction to obtain a membrane (I') with a diameter from 6 mm to 16 mm and a radius of curvature from 6 mm to 8 mm after cutting and drying. Herein, the result was disposed in a chamber under the saturated vapor pressure of formaldehyde for 1 hour to undergo the cross-linking reaction.

EXAMPLE 2

First, 0.5 g of collagen (strip-shaped fiber with a fiber length about 15 mm), and 100 mL of an aqueous solution (pH<5) were added into a reaction bottle. Next, after the collagen was dissolved into the water, the solution was injected into a two-dimensional mold and dried at room temperature. Next, a part of the result was disposed in a chamber to undergo a cross-linking reaction and cut to obtain a membrane (II) with a diameter from 6 mm to 16 mm. Furthermore, another part of the result was also disposed into a mold (having a radius of curvature from 6 mm to 8 mm) after swelling with water, and then underwent a cross-linking reaction to obtain a membrane (II') with a diameter from 6 mm to 16 mm and a radius of curvature from 6 mm to 8 mm after cutting and drying. Herein, the result was disposed in a chamber and irradiated by an ultraviolet light with a wavelength of 254 nm and an intensity of 3 mW/cm$^2$ for 1 hour to undergo the cross-linking reaction.

EXAMPLE 3

First, 0.5 g of polyvinyl alcohol (PVA, with a molecular weight about 30,000-50,000), and 100 mL of water were added into a reaction bottle. Next, after the collagen was dissolved into the water, HCl aqueous solution (6N) was added into the reaction bottle, obtaining a solution with a pH lower than 3. Next, 0.5 g of collagen (strip-shaped fiber with a fiber length about 15 mm) was added into the reaction bottle. Next, after the collagen was dissolved into the water, the solution was injected into a two-dimensional mold and dried at room temperature. Next, a part of the result was disposed in a chamber to undergo a cross-linking reaction and cut to obtain a membrane (III) with a diameter from 6 mm to 16 mm. Furthermore, another part of the result was also disposed into a mold (having a radius of curvature from 6 mm to 8 mm) after swelling with water, and then underwent a cross-linking reaction to obtain a membrane (III') with a diameter from 6 mm to 16 mm and a radius of curvature from 6 mm to 8 mm after cutting and drying. Herein, the result was disposed in a chamber under the saturated vapor pressure of formaldehyde for 1 hour to undergo the cross-linking reaction.

EXAMPLE 4

First, 0.5 g of polyethylene glycol/polyethylene oxide (PEG/PEO with a molecular weight about 30,000-70,000), and 100 mL of water were added into a reaction bottle. Next, after the collagen was dissolved into the water, HCl aqueous solution (6N) was added into the reaction bottle, obtaining a solution with a pH lower than 3. Next, 0.5 g of collagen (strip-shaped fiber with a fiber length about 15 mm) was added into the reaction bottle. Next, after the collagen was dissolved into the water, the solution was injected into a two-dimensional mold and dried at room temperature. Next, a part of the result was disposed in a chamber to undergo a cross-linking reaction and cut to obtain a membrane (IV) with a diameter from 6 mm to 16 mm. Furthermore, another part of the result was also disposed into a mold (having a radius of curvature from 6 mm to 8 mm) after swelling with water, and then underwent a cross-linking reaction to obtain a membrane (IV') with a diameter from 6 mm to 16 mm and a radius of curvature from 6 mm to 8 mm after cutting and drying. Herein, the result was disposed in a chamber under the saturated vapor pressure of formaldehyde for 1 hour to undergo the cross-linking reaction.

EXAMPLE 5

First, 0.5 g of polyvinylpyrrolidone (PVP with a molecular weight about 58,000), and 100 mL of water were added into a reaction bottle. Next, after the collagen was dissolved into the water, HCl aqueous solution (6N) was added into the reaction bottle, obtaining a solution with a pH lower than 3. Next, 0.5 g of collagen (strip-shaped fiber with a fiber length about 15 mm) was added into the reaction bottle. Next, after the collagen was dissolved into the water, the solution was injected into a two-dimensional mold and dried at room temperature. Next, a part of the result was disposed in a chamber to undergo a cross-linking reaction and cut to obtain a membrane (V) with a diameter of 12 mm. Furthermore, another part of the result was also disposed into a mold (having a radius of curvature from 6 mm to 8 mm) after swelling with water, and then underwent a cross-linking reaction to obtain a membrane (V') with a diameter of 12 mm and a radius of curvature from 6 mm to 8 mm after cutting and drying. Herein, the result was disposed in a chamber under the saturated vapor pressure of formaldehyde for 1 hour to undergo the cross-linking reaction.

Figure 1A:
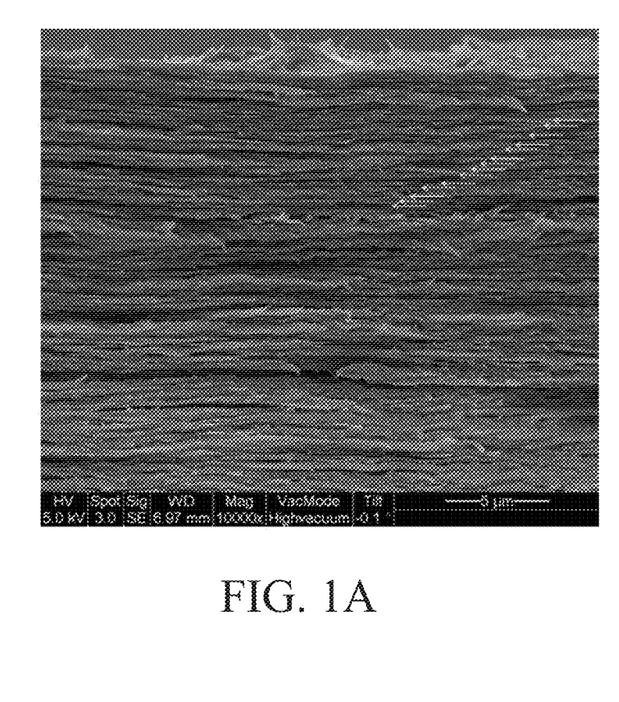
FIG. 1A is a scanning electron microscope (SEM) photograph of the membrane according to an embodiment of the disclosure.

The membrane (V) and (V') were observed by a scanning electron microscope, and the result is shown in FIG. 1A, wherein arrows in FIG. 1A point out the stacked layers. As shown in FIG. 1A, the membrane (V) has a multi-layered structure.

EXAMPLE 6

First, 0.5 g of polyvinylpyrrolidone (PVP with a molecular weight about 58,000), and 100 mL of water were added into a reaction bottle. Next, after the collagen was dissolved into the water, HCl aqueous solution (6N) was added into the reaction bottle, obtaining a solution with a pH lower than 3. Next, 0.5 g of collagen (strip-shaped fiber with a fiber length about 15 mm) was added into the reaction bottle. Next, after the collagen was dissolved into the water, the solution was injected into a two-dimensional mold and dried at room temperature. Next, a part of the result was disposed in a chamber to undergo a cross-linking reaction and cut to obtain a membrane (VI) with a diameter from 6 mm to 16 mm. Furthermore, another part of the result was also disposed into a mold (having a radius of curvature from 6 mm to 8 mm) after swelling with water, and then underwent a cross-linking reaction to obtain a membrane (VI') with a diameter from 6 mm to 16 mm and a radius of curvature from 6 mm to 8 mm after cutting and drying. Herein, the result was disposed in a chamber and irradiated by an ultraviolet light with a wavelength of 254 nm and an intensity of 3 mW/cm$^2$ for 1 hour to undergo the cross-linking reaction.

EXAMPLE 7

First, 0.5 g of polyvinylpyrrolidone (PVP with a molecular weight about 58,000), and 100 mL of water were added into a reaction bottle. Next, after the collagen was dissolved into the water, HCl aqueous solution (6N) was added into the reaction bottle, obtaining a solution with a pH lower than 3. Next, 0.5 g of collagen (flocculent fiber with a maximum length lower than 1.5 mm) was added into the reaction bottle. Next, after the collagen was dissolved into the water, the solution was injected into a two-dimensional mold and dried at room temperature. Next, a part of the result was disposed in a chamber to undergo a cross-linking reaction and cut to obtain a membrane (VII) with a diameter from 6 mm to 16 mm. Furthermore, another part of the result was also disposed into a mold (having a radius of curvature from 6 mm to 8 mm) after swelling with water, and then underwent a cross-linking reaction to obtain a membrane (VII') with a diameter from 6 mm to 16 mm and a radius of curvature from 6 mm to 8 mm after cutting and drying. Herein, the result was disposed in a chamber under the saturated vapor pressure of formaldehyde for 1 hour to undergo the cross-linking reaction.

Figure 1B:
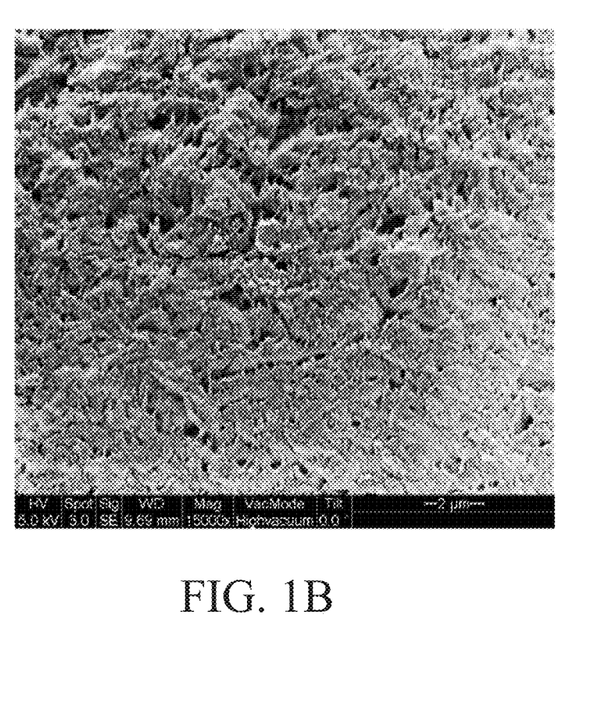
FIG. 1B is a scanning electron microscope (SEM) photograph of the membrane according to another embodiment of the disclosure.

The membrane (VII) and (VII') were observed by a scanning electron microscope, and the result is shown in FIG. 1B. As shown in FIG. 1B, the film (VII) does not have a multi-layered structure since the collagen has flocculent fibers with a maximum length lower than 1.5 mm.

EXAMPLE 8

First, 0.5 g of polyvinylpyrrolidone (PVP with a molecular weight about 58.000), and 100 mL of water were added into a reaction bottle. Next, after the collagen was dissolved into the water, HCl aqueous solution (6N) was added into the reaction bottle, obtaining a solution with a pH lower than 3. Next, 0.5 g of collagen (gel-type) was added into the reaction bottle. Next, after the collagen was dissolved into the water, the solution was injected into a two-dimensional mold and dried at room temperature. Next, a part of the result was disposed in a chamber to undergo a cross-linking reaction and cut to obtain a membrane (VIII) with a diameter from 6 mm to 16 mm. Furthermore, another part of the result was also disposed into a mold (having a radius of curvature from 6 mm to 8 mm) after swelling with water, and then underwent a cross-linking reaction to obtain a membrane (VIII') with a diameter from 6 mm to 16 mm and a radius of curvature from 6 mm to 8 mm after cutting and drying. Herein, the result was disposed in a chamber under the saturated vapor pressure of formaldehyde for 1 hour to undergo the cross-linking reaction.

EXAMPLE 9

First, 0.5 g of polyvinyl alcohol (PVA, with a molecular weight about 30,000-50,000), and 100 mL of water were added into a reaction bottle. Next, after the collagen was dissolved into the water, HCl aqueous solution (6N) was added into the reaction bottle, obtaining a solution with a pH lower than 3. Next, 0.5 g of collagen (flocculent fiber with a maximum length lower than 1.5 mm) was added into the reaction bottle. Next, after the collagen was dissolved into the water, the solution was injected into a two-dimensional mold and dried at room temperature. Next, a part of the result was disposed in a chamber to undergo a cross-linking reaction and cut to obtain a membrane (IX) with a diameter from 6 mm to 16 mm. Furthermore, another part of the result was also disposed into a mold (having a radius of curvature from 6 mm to 8 mm) after swelling with water, and then underwent a cross-linking reaction to obtain a membrane (IX') with a diameter from 6 mm to 16 mm and a radius of curvature from 6 mm to 8 mm after cutting and drying. Herein, the result was disposed in a chamber under the saturated vapor pressure of formaldehyde for 1 hour to undergo the cross-linking reaction.

EXAMPLE 10

First, 0.5 g of polyethylene glycol/polyethylene oxide (PEG/PEO with a molecular weight about 30,000-70,000), and 100 mL of water were added into a reaction bottle. Next, after the collagen was dissolved into the water, HCl aqueous solution (6N) was added into the reaction bottle, obtaining a solution with a pH lower than 3. Next, 0.5 g of collagen (flocculent fiber with a maximum length lower than 1.5 mm)

was added into the reaction bottle. Next, after the collagen was dissolved into the water, the solution was injected into a two-dimensional mold and dried at room temperature. Next, a part of the result was disposed in a chamber to undergo a cross-linking reaction and cut to obtain a membrane (X) with a diameter from 6 mm to 16 mm. Furthermore, another part of the result was also disposed into a mold (having a radius of curvature from 6 mm to 8 mm) after swelling with water, and then underwent a cross-linking In addition, the suture pull-out strength of the film was measured using the following steps: First, the film was cut into a test piece with a size of 20 mm×50 mm. After the test piece was placed in water for 20 minutes, a suture was threaded through the test piece (with a thickness between 50 μm and 500 μm when swelling with water) in a location wherein the distance between the location and a boundary of the test piece was 10 mm. The suture was pulled at about 10 mm/min via a tensile tester, thereby measuring the stress.

TABLE 1

| membrane | collagen fiber length (mm) | polymer | treatment | thickness (μm)(after swelling with water) | swelling ratio | suture pull-out strength (MPa) | light transmittance (%) |
| --- | --- | --- | --- | --- | --- | --- | --- |
| (I)/(I') | ~15 | | formaldehyde gas | 150.1 | 6.7 | 29.0 | >85% |
| (II)/(II') | ~15 | | ultraviolet light | 124.3 | 1.4 | 28.7 | >85% |
| (III)/(III') | ~15 | PVA (30,000-50,000) | formaldehyde gas | — | — | — | >90% |
| (IV)/(IV') | ~15 | PEG (30,000-70,000) | formaldehyde gas | — | — | — | >90% |
| (V)/(V') | ~15 | PVP | formaldehyde gas | 223.7 | 9.5 | 20.0 | >95% |
| (VI)/(VI') | ~15 | PVP | ultraviolet light | 185.1 | 2.1 | 8.8 | >85% |
| (VII)/(VII') | flocculence/<1.5 | PVP | formaldehyde gas | 270 | 1.9 | 2.9 | >95% |
| (VIII)/(VIII') | gel-type | PVP | formaldehyde gas | — | — | — | opacity |
| (IX)/(IX') | flocculence/<1.5 | PVA (30,000-50,000) | formaldehyde gas | — | — | — | <60% |
| (X)/(X') | flocculence/<1.5 | PEG (30,000-70,000) | formaldehyde gas | — | — | — | <90% | reaction to obtain a membrane (X') with a diameter from 6 mm to 16 mm and a radius of curvature from 6 mm to 8 mm after cutting and drying. Herein, the result was disposed in a chamber under the saturated vapor pressure of formaldehyde for 1 hour to undergo the cross-linking reaction.

Measurement of the Membrane

EXAMPLE 11

The light transmittance, swelling ratio, and suture pull-out strength of the membranes (I)-(X) and (I')-(X') of Examples 1-10 were measured, and the results are shown in Table 1.

The light transmittance of the film was determined by measuring the light absorption coefficient in the wavelength range of 350 nm to 700 nm of the film (having a saturated water content) via a spectrophotometer and measuring the light transmittance by means of the light absorption coefficient.

The swelling ratio of the film was measured using the following steps. First, the weight of the dry film (W1) was measured. Next, the dry film was placed in water for 20 minutes, and then the weight of the swelling film (W2) was measured. Next, the swelling ratio was determined using the following equation:

$$\text{swelling ratio} = \frac{(W2 - W1)}{W1} \times 100\%.$$

As shown in Table 1, since the membranes (III)-(V) and (III')-(V') of Example 3-5 include the polymer (such as polyvinyl alcohol (PVA), polyethylene glycol/polyethylene oxide (PEG/PEO), or polyvinylpyrrolidone), the membranes (III)-(V) and (III')-(V') (swollen with water) have a greater light transmittance than 90%. In addition, due to the use of collagen with a fiber length that is longer than 15 mm, the membranes (III) and (III') (swollen with water) have a higher light transmittance than about 90%. In comparison, the membranes (IX), (IX'), (X), and (X') without the strip-shaped fiber have a light transmittance lower than 90%, even lower than 60%. The method for fabricating the membranes (V) and (V') has a cross-linking process different from that of the method for fabricating the membranes (VI) and (VI'). As shown in Table 1, the suture pull-out strength of the membranes (V), (V'), (VI) and (VI') of Examples 5 and 6 are both greater than 8 MPa. Moreover, since the collagen used in Example 5 has a longer fiber length than that used in Example 7, the membranes (V) and (V') have a multi-layered structure (as shown in FIG. 1) and have a suture pull-out strength of about 20 MPa. Due to the flocculent fiber, the membranes (VII) and (VII') do not have a multi-layered structure (FIG. 2), and have a suture pull-out strength of about 2.9 MPa. Furthermore, due to the use of gel-type collagen rather than strip-shaped collagen fiber, the membranes (VIII) and (VIII') of Example 8 are opaque after swelling with water.

Accordingly, since the collagen used for preparing the membrane of the disclosure is strip-shaped fiber (having a fiber length between about 1.5 mm and 50 mm), the membrane of the disclosure can have a multi-layered structure. Therefore, the membrane exhibits a high swelling ratio, high suture pull-out strength, and high light transmittance. Furthermore, the membrane of the disclosure can be applied to ophthalmology, surgical use, or tissue engineering.

Comparison of the membrane of the disclosure and the commercial ocular viscoelastic devices (OVD)

EXAMPLE 12

In order to determine whether the membranes of Examples of the disclosure meet the requirement of protecting corneal endothelial cells, the membrane (V') of Example 5 and the commercial ocular viscoelastic devices (VISCOAT) were used in implantation of animal model experiment as following. The process and location of implantation can refer to the flow chart of FIG. 2A and the schematic diagram of FIG. 2B.

Figure 2C:
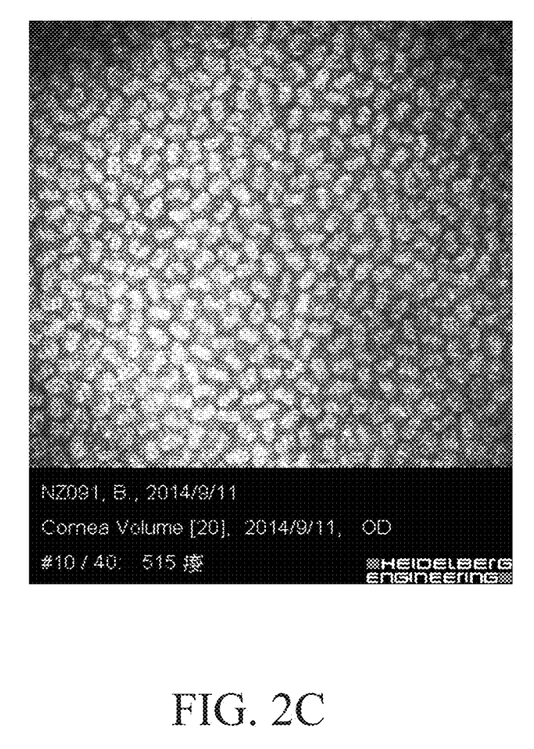
FIG. 2C is a confocal microscope image showing the corneal endothelial cells of a white rabbit, wherein a membrane of an embodiment of the disclosure is disposed in the corneal endothelial cells of the white rabbit.
Figure 2D:
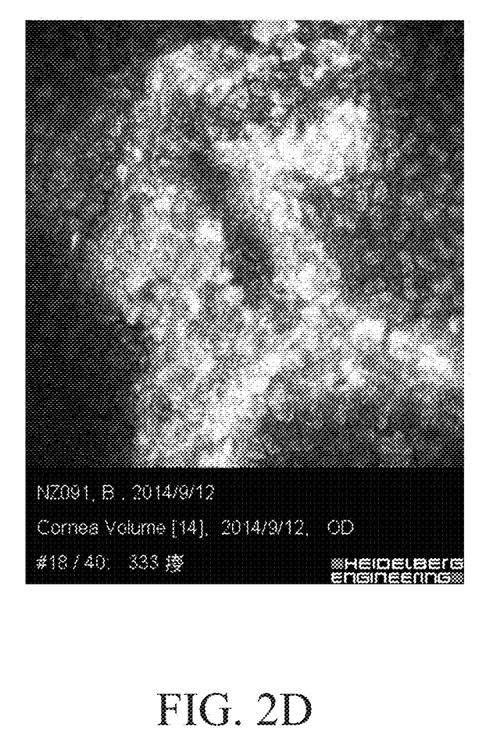
FIG. 2D is a confocal microscope image showing the corneal endothelial cells of a white rabbit, wherein the commercial ocular viscoelastic device is disposed in the corneal endothelial cells of the white rabbit.

First, New Zealand white rabbits were used as subjects of animal model experiment. The eye of the white rabbit was subjected to a minimally invasive surgery to yield a wound with a diameter of 2.2 mm. Next, the membrane (V') for protecting intraocular tissues of Example 5 was implanted into the eye of the white rabbit of the experimental group. After swelling with water, the membrane (V') had a light transmittance greater than 95%, a water retention of 90%, a diameter of 12 mm, a radius of curvature from 6 mm to 8 mm, and a thickness of about 200 µm. On the other hand, the commercial ocular viscoelastic device (VISCOAT) was implanted into the eye of the white rabbit of the control group. Next, the white rabbits of the experimental group and the control group were subjected to cataract surgery. The natural crystalline lens of the white rabbits were removed during the phacoemulsification having an operating period of 7 minutes. Next, the membrane (V') of the white rabbit of the experimental group and the commercial ocular viscoelastic device of the white rabbit of the control group were removed, and the wounds of the white rabbits were sutured. Next, the corneal endothelial cells of the white rabbit of the experimental group and control group were observed by the in vivo confocal microscope at once and after 1, 2, and 7 days. FIG. 2C is the confocal microscope image showing the corneal endothelial cells of a white rabbit (experimental group), wherein a membrane of an embodiment of the disclosure is disposed in the corneal endothelial cells of the white rabbit, and FIG. 2D is the confocal microscope image showing the corneal endothelial cells of a white rabbit, wherein the commercial ocular viscoelastic device is disposed in the corneal endothelial cells of the white rabbit. As shown in FIGS. 2C and 2D, the commercial ocular viscoelastic device substantially damages the corneal endothelial cells; on the contrary, the membrane (V') of the disclosure indeed achieves the purpose of protecting the corneal endothelial cells.

It will be clear that various modifications and variations can be made to the disclosed methods and materials. It is intended that the specification and examples be considered as exemplary only, with the true scope of the disclosure being indicated by the following claims and their equivalents.

What is claimed is:

1. A membrane for protecting intraocular tissues, comprising a multi-layered structure composed of a collagen and a hydrophilic polymer,
    wherein the collagen is strip-shaped and has a fiber length between about 15 mm and 50 mm,
    wherein the membrane has a diameter between 6 mm and 16 mm, and the membrane in a dry state has a first thickness between 5 µm and 100 µm, and
    wherein the hydrophilic polymer is polyethylene glycol, polyethylene oxide, polyvinyl alcohol, polyvinylpyrrolidone, or a combination thereof.

2. The membrane for protecting intraocular tissues as claimed in claim 1, wherein the hydrophilic polymer has a weight-average molecular weight from 300 to 400,000.

3. The membrane for protecting intraocular tissues as claimed in claim 1, wherein the weight ratio between the collagen and the hydrophilic polymer is from 1:3 to 9:1.

4. The membrane for protecting intraocular tissues as claimed in claim 1, wherein the membrane has a curved surface, and the curved surface has a radius of curvature from 6 mm to 8 mm.

5. The membrane for protecting intraocular tissues as claimed in claim 1, wherein the membrane is a transparent membrane after swelling with water.

6. The membrane for protecting intraocular tissues as claimed in claim 5, wherein the transparent membrane has a second thickness from 50 µm to 300 µm.

7. The membrane for protecting intraocular tissues as claimed in claim 5, wherein the transparent membrane has a water retention greater than or equal to 80%.

8. The membrane for protecting intraocular tissues as claimed in claim 5, wherein the transparent membrane has a light transmittance greater than or equal to 90%.

9. A method for protecting corneal endothelial cells, comprising:
    providing the membrane for protecting intraocular tissues as claimed in claim 1, wherein the membrane has a curved surface, and the curved surface has a radius of curvature from 6 mm to 8 mm;
    allowing the membrane for protecting intraocular tissues to be swollen after swelling with water, obtaining a transparent membrane having a thickness between 50 µm and 300 µm;
    disposing the transparent membrane in an anterior capsule to cover corneal endothelial cells.

10. The method as claimed in claim 9, wherein the transparent membrane has a water retention greater than or equal to 80%.

11. The method as claimed in claim 9, wherein the transparent membrane has a light transmittance greater than or equal to 90%.

12. The method as claimed in claim 9, further comprising:
    removing the transparent membrane from the anterior capsule.

13. A method for protecting intraocular tissues, comprising:
    providing the membrane for protecting intraocular tissues as claimed in claim 1;
    allowing the membrane for protecting intraocular tissues to be swollen after swelling with water, obtaining a transparent membrane having a thickness between 50 µm and 300 µm; and
    disposing the transparent membrane in front of the posterior capsule of a crystalline lens.

14. The method as claimed in claim 13, wherein the transparent membrane has a water retention greater than or equal to 80%.

15. The method as claimed in claim 13, wherein the transparent membrane has a light transmittance greater than or equal to 90%.

16. The method as claimed in claim 13, further comprising:
    removing the transparent membrane from the front of the posterior capsule.

* * * * *